US00PP11675P

United States Patent [19]

Noodelijk

[11] Patent Number: Plant 11,675

[45] Date of Patent: Dec. 12, 2000

[54] CHRYSANTHEMUM PLANT NAMED 'WHITE REFOCUS'

[75] Inventor: Robert Noodelijk, Woubrugge, Netherlands

[73] Assignee: Chrysanthemum Breeders Association N.V., Netherlands

[21] Appl. No.: 09/149,657

[22] Filed: Sep. 9, 1998

[51] Int. Cl.[7] ..... A01H 5/00

[52] U.S. Cl. ..... Plt./294

[58] Field of Search ..... Plt./294

[56] References Cited

PUBLICATIONS

UPOV–ROM, 1992/02, Plant Variety Database, GTI Jouve Retrieval Software, citation for 'White Refocus'.

UPOV–ROM, 1999/02, Plant Variety Database, GTI Jouve Retrieval Software, 2 citations for 'Red Refocus'.

*Primary Examiner*—Howard J. Locker

[57] ABSTRACT

A chrysanthemum plant named WHITE REFOCUS characterized by its small blooms with white ray florets and green-yellow disc florets.

2 Drawing Sheets

The present plant is related to the plants of the following co- pending applications:

| Application no. | Filing Date | Title |
|---|---|---|
| 09/149,300 | 09/09/98 | Refocus |
| 09/149,299 | 09/09/98 | Pink Refocus |
| 09/149,460 | 09/09/98 | Red Refocus |

BACKGROUND OF THE INVENTION

The present invention comprises a new a distinct cultivar of chrysanthemum plant that is a natural occuring sport of a parent chrysanthemum named Refocus. Parent chrysanthemum Refocus is also described in this application. The new cultivar was discovered as a whole plant mutation in May, 1995 by Rob Noodelijk in a greenhouse in Rijsenhout, Holland.

The first act of asexual reproduction of WHITE REFOCUS was accomplished when vegetative cuttings were taken from the initial selection in August, 1995 in a controlled environment in Ter Aar, Holland.

SUMMARY OF THE INVENTION

The present invention is a new and distinct variety of chrysanthemum bearing a small sized bloom with white ray florets and green-yellow disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
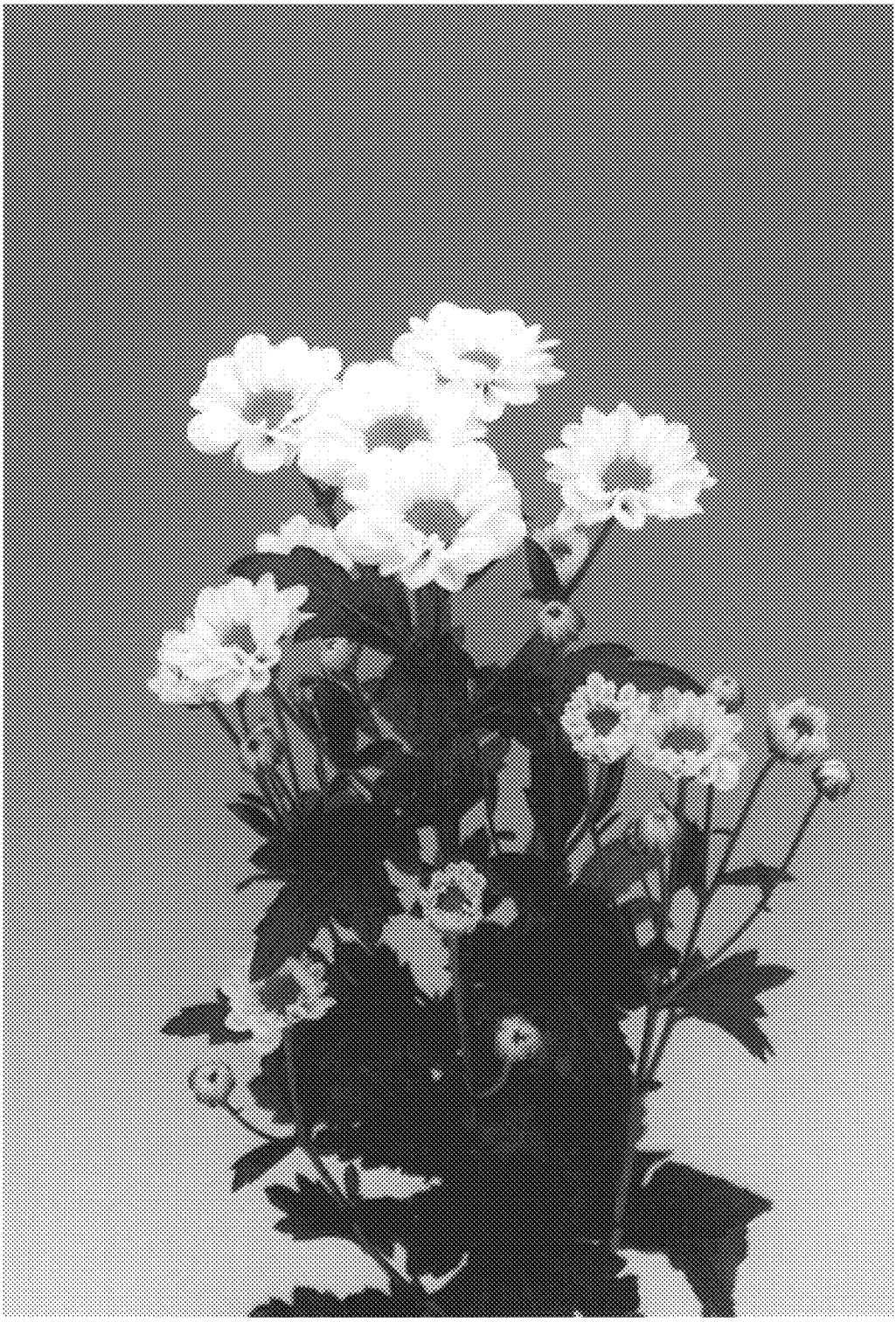
FIG. 1 shows the stem of the cultivar in full bloom.
Figure 2:
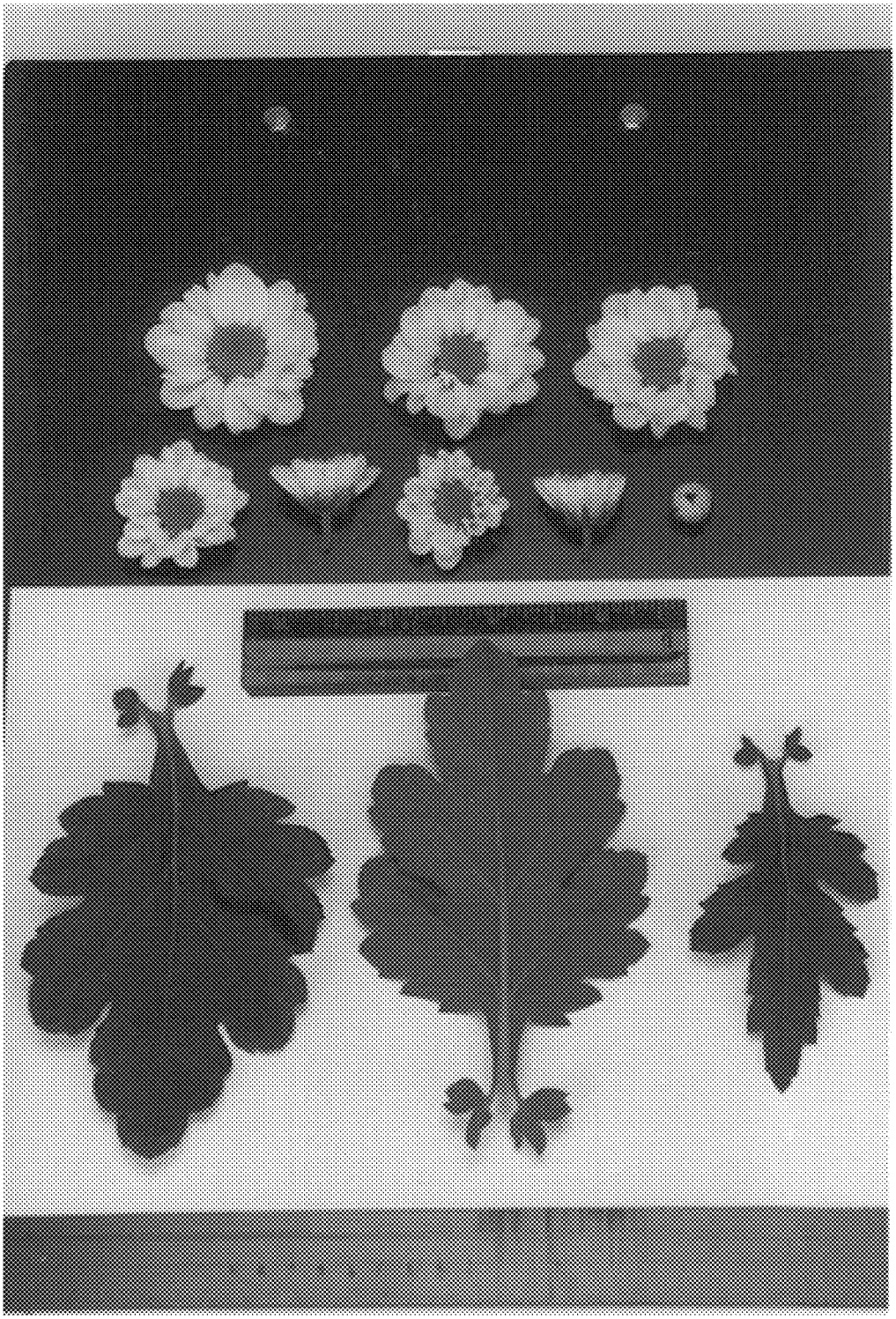
FIG. 2 shows the various stages of bloom and foliage of the new cultivar.

This new variety of chrysanthemum is of the botanical classification *Dendranthema grandiflora*. When grown in the vicinity of Rijsenhout, Holland, it has a response time of approximately 8 weeks. This new variety produces small sized blooms with white ray florets and green-yellow disc florets having a 3 week performance (i.e, vase life of 21 days). This new variety of chrysanthemum has been found to retain its distinctive characteristics throughout successive propagations. However, the phenotype may vary significantly with variations in environment such as light intensity and temperature. To show the phenotype as described, White Refocus may be planted year round under green house conditions in Holland. The following is a description of the plant and characteristics that distinguish White Refocus as a new and distinct variety.

The color designations are taken from the plant itself. Accordingly, any discrepancies between the color designations and the colors depicted in the photographs are due to photographic tolerances.

| CULTIVAR | WHITE REFOCUS | Parent Cultivar REFOCUS |
|---|---|---|
| Bud | | |
| Size | medium cross section ±1.5 cm, height ±1.0 cm | medium, cross section ±1.2 cm, height ±1.2 cm |
| Outside Color | yellow-orange 20D | red-purple 70A |
| Bloom | | |
| Size | small | small |
| Fully Expanded | 3½–4 cm | 4–4½ cm |
| Borne | upper portion single flower per peduncle, lower portion plural flower per peduncle | upper portion single flower per peduncle, lower portion plural flower perpeduncle |
| Number of Blooms (per single stem) | average of 10 | average of 10 |
| Peduncle Lengths | near the top ±10 cm, near the middle 20 cm, near the bottom 20 cm. | near the top ±10 cm, near the middle 20 cm, near the bottom 20 cm. |
| Peduncle Lateral Shoot, Attachment | medium | medium to strong |
| Peduncle Lateral Shoot, Angle | 30°–35° | 30°–35° |
| Form | single (daisy) | single (daisy) |
| Performance (blooming period) | good, 21 days (18°–20° C.) | good, 21 days (18°–20° C.) |
| Color | | |
| Center of Flower/disc floret | yellow-green 144A at an early stage of inflorescence, mature yellow-orange 14B | yellow-green 145A at an early stage of inflorescence, mature yellow-orange 14B |

-continued

| | | |
|---|---|---|
| Color of upper surface of the majority of the ray-florets | pure white 155D (but whiter) | red-purple 71C |
| Color of the lower surface of the majority of the ray-florets | pure white 155D (but whiter) | purple violet 80 D |
| Tonality from Distance | a clear white small daisy | a small purple daisy |
| Discoloration | ray florets none, disc florets to yellow-orange 14B | ray-florets to red-purple 72D disc-floret to yellow-orange 14B |
| Pollen | none | yellow-orange 14A |
| Ray florets | | |
| Texture | upperside smooth, underside smooth | upperside smooth, underside smooth |
| Number | 22–26 (2 rows) | 35–40 (2–3 rows) |
| Cross-section | convex (no keels) | concave |
| Longitudinal axis of majority | reflexing | straight |
| Shape of tip | rounded | pointed |
| Fragrance | typical chrysanthemum | typical chrysanthemum |
| Disc Diameter | small to medium (1.2–15 cm) | small to medium (1.0–1.2 cm) |
| Stamen (present in disc florets only) | yellow-green, thin, ±4 mm in length | yellow-green, thin, ±4 mm in length |
| Pollen | none | present, abundant |
| Styles (present in both ray and disc florets) | yellow-green, thin | yellow-green, thin |
| Style Length | ±4 mm | ±4 mm |
| Stigmas | yellow | yellow |
| Stigma Width | ±1 mm | ±1 mm |
| Ovaries | enclosed in calyx | enclosed in calyx |
| Plant | | |
| Form | spray mum meant for erect culture. Herbaceous | spray mum meant for erect culture. Herbaceous |
| Growth | short to medium | short to medium |
| Height | ±100–105 cm | ±95–100 cm |
| Stem Color | yellow-green 147B | yellow-green 146B |
| Stem Strength | strong | strong |
| Stem Brittleness | present | present |
| Stem Anthocyanin Coloration | present | absent |
| Internodes | short (1.5–2.0 cm) | short (1.5–2.0 cm) |
| Flowering Response (photoperiodic controlled crop, no natural growing) | 8 weeks | 8 weeks |
| Foliage | | |
| Color | upperside yellow-green 147A underside yellow-green 147B | upperside yellow-green 147A underside yellow-green 147B |
| Size | length 9 cm; width 6 cm | length 9 cm; width 6 cm |
| Quantity (per single stem) | 30–35 | 28–32 |
| Shape | egg-shaped | egg-shaped |
| Texture | fleshy | fleshy |
| Ribs and Veins | both ribs and veins well developed | both ribs and veins well developed |
| Edge | crenated | crenated |
| Shape of Base of Sinus Between Lateral Lobes | round | round |
| Margin of Sinus Between Lateral Lobes | converging | converging |
| Shape of Base | truncated | rounded |
| Apex | mucronate | mucronate |
| Growth | | |

-continued

| Year of Discovery | 1995 | 1992 |
|---|---|---|
| CULTIVAR | PINK REFOCUS | RED REFOCUS |
| Bud | | |
| Size | medium, cross section ±1.2 cm, height ±1.2 cm | small cross section ±1.0 cm, Height ±1.2 cm |
| Outside Color | red-purple 58B | Red 46B |
| Bloom | | |
| Size | small | small |
| Fully Expanded | 4½–5 cm | 4–4½ cm |
| Borne | upper portion single flower perpeduncle, lower portion plural flower per peduncle | upper portion single flower per peduncle, lower portion plural flower per peduncle |
| Number of Blooms (per single stem) | average of 10 | average of 10 |
| Peduncle Lengths | near the top ±10 cm, near the middle 20 cm, near the bottom 20 cm. | near the top ±10 cm, near the middle 20 cm, near the bottom 20 cm. |
| Peduncle Lateral Shoot, Attachment | medium to strong | medium |
| Peduncle Lateral Shoot, Angle | 30°–35° | 30° |
| Form | single (daisy) | single (daisy) |
| Performance (blooming period) | good, 21 days (18°–20° C.) | good, 21 days (18°–20° C.) |
| Color | | |
| Center of Flower/disc floret | yellow-green 144B at an early stage of inflorescence, mature yellow-orange 14B | yellow-green 144B at an early stage of inflorescence, mature yellow-orange 14B |
| Color of upper surface of the majority of the ray-florets | near red-purple 58C | red 45A |
| Color of the lower surface of the majority of the ray-florets | red-purple 58C | red 45C |
| Tonality from Distance | a small pink/purple daisy | a small red daisy |
| Discoloration | ray-florets to red-purple 58D disc-floret to yellow-orange 14B | ray-florets to red 45C disc-floret to yellow-orange 14B |
| Pollen | yellow-orange 14A | yellow-orange 14A |
| Ray florets | | |
| Texture | upperside smoth, underside smooth | upperside smooth, underside smooth |
| Number | 38–45 (3 rows) | 35–40 (2–3 rows) |
| Cross-section | concave | concave |
| Longitudinal axis of majority | straight | straight |
| Shape of tip | pointed | pointed |
| Fragrance | typical chrysanthemum | typical chrysanthemum |
| Disc Diameter | small to medium (1.0–1.2 cm) | small to medium (1.0–1.2 cm) |
| Stamen (present in disc florets only) | yellow-green, thin, ±4 mm in length | yellow-green, thin, ±4 mm in length |
| Pollen | Present, abundant | Present, abundant |
| Styles (present in both ray and disc florets) | yellow-green, thin | yellow-green, thin |
| Style Length | ±4 mm | ±4 mm |
| Stigmas | yellow | yellow |
| Stigma Width | ±1 mm | ±1 mm |
| Ovaries | enclosed in calyx | enclosed in calyx |
| Plant | | |
| Form | spray mum meant for erect culture. Herbaceous | spray mum meant for erect culture. Herbaceous |
| Growth | short to medium | short to medium |
| Height | ±100–105 cm | ±95–100 cm |
| Stem Color | yellow-green 146B | yellow-green 146B |
| Stem Strength | strong | strong |

-continued

| | | |
|---|---|---|
| Stem Brittleness | absent | absent |
| Stem Anthocyanin Coloration | present | present |
| Internodes | short (1.5–2.0 cm) | short (1.5–2.0 cm) |
| Flowering Response (photoperiodic controlled crop, no natural growing) | 8 weeks | 8 weeks |
| Foliage | | |
| Color | upperside yellow-green 147A underside yellow-green 147B | upperside yellow-green 147A underside yellow-green 147B |
| Size | length 9 cm; width 6 cm | length 10 cm; width 7 cm |
| Quantity (per single stem) | 28–32 | 28–32 |
| Shape | egg-shaped | egg-shaped |

-continued

| | | |
|---|---|---|
| Texture | fleshy | fleshy |
| Ribs and Veins | both ribs and veins well developed | both ribs and veins well developed |
| Edge | crenated | crenated |
| Shape of Base of Sinus Between Lateral Lobes | round | round |
| Margin of Sinus Between Lateral Lobes | converging | converging |
| Shape of Base | obtuse | truncated |
| Apex | cuspidate | mucronate |
| Growth | | |
| Year of Discovery | 1993 | 1993 |

I claim:

1. A new and distinct variety of chrysanthemum plant as described and illustrated.

* * * * *